United States Patent [19]

Berger

[11] Patent Number: 5,179,963
[45] Date of Patent: Jan. 19, 1993

[54] PERCUTANEOUS CARPAL TUNNEL PLASTY METHOD

[76] Inventor: J. Lee Berger, 895 Mohawk Rd., Franklin Lakes, N.J. 07417

[21] Appl. No.: 774,869

[22] Filed: Oct. 11, 1991

[51] Int. Cl.⁵ .......................................... A61B 17/00
[52] U.S. Cl. ................................. 128/898; 606/192
[58] Field of Search ................ 606/192; 604/96; 128/898

[56] References Cited

U.S. PATENT DOCUMENTS

| | | | |
|---|---|---|---|
| 2,164,928 | 7/1939 | Kleine | 128/349 |
| 3,537,452 | 11/1970 | Wilks | 128/214.4 |
| 3,559,643 | 2/1971 | Pannier et al. | 128/214.4 |
| 3,592,193 | 7/1971 | Higgins | 128/214.4 |
| 4,250,881 | 2/1981 | Smith | 128/214.4 |
| 4,645,491 | 2/1987 | Evans | 604/158 |
| 4,655,214 | 4/1987 | Linder | 128/207.18 |
| 4,962,770 | 10/1990 | Agee et al. | 128/898 |
| 5,011,478 | 4/1991 | Cope | 604/165 |
| 5,029,573 | 7/1991 | Chow | 606/170 |

Primary Examiner—David A. Wiecking
Assistant Examiner—Ren Yan
Attorney, Agent, or Firm—John S. Hale

[57] ABSTRACT

Nerve entrapment such as Carpal Tunnel Syndrome is relieved by a surgical procedure for increasing the spatial diameter of the tunnel enclosing the nerve, which involves inserting a protected balloon catheter into the tunnel and serially inflating and deflating the catheter while moving it along the tunnel from one end to the other.

9 Claims, 4 Drawing Sheets

PERCUTANEOUS CARPAL TUNNEL PLASTY METHOD

BACKGROUND OF THE INVENTION invention is directed to a surgical procedure for relieving nerve entrapment such as Carpal Tunnel Syndrome by increasing the spatial diameter of the tunnel enclosing the nerve.

Carpal Tunnel Syndrome is a common painful condition of the hand characterized by a decrease in median nerve sensibility with paresthesias of the fingers. It is the most common nerve entrapment syndrome of the upper extremity and results from compression of the median nerve in the carpal tunnel and provides nocturnal pain, clumsiness, and weakness of grasp or pinch.

The carpal canal is the area in the wrist and palm of the hand formed by the U-shaped cluster of bones of the carpus that forms the rigid hard floor and the two sides of the tunnel. Within the confines of this space are the median nerve, and the extrinsic flexor tendons of the thumb and fingers with their surrounding synovial membranes of the radial and ulna brusae. The roof of the tunnel is formed by the transverse carpal ligament on the palmar surface of the carpal bones. The ligament is attached medially to the pisiform and the hamulus of the hamate and laterally to the tuberosity of the scaphoid and the medial part of the palmar surface and ridge of the trapezium. The proximal border of the ligament is partially merged to the distal border of the palmar carpal ligament, but this is a more superficial structure and is separated from it by the ulnar artery and nerve. The transverse carpal ligament is attached to the palmar aponeurosis, which lies superficial, and contributes crossed oblique fibers to the deep surface of the aponeurosis. (Goss, Charles Mayo Ed.; Gray's Anatomy; Twenty-ninth American Edition, p 473.)

Any condition that diminishes the size of the carpal tunnel can precipatate the Carpal Tunnel Syndrome (Milford, Lee., Campbell's Operative Orthopaedics., 7th Ed: 459). Repetitive wrist and hand motions can cause thickening and hypertrophy of the transverse carpal ligament. Also, proliferation of synovium from normal wear and tear of daily activities can cause compression of the median nerve within the closed confines of the carpal tunnel. A previous fracture or dislocation of the wrist may cause bone to protrude with narrowing of the tunnel. Furthermore, systemic conditions such as pregnancy, obesity, diabetes, mellitus, thyroid dysfunction, or chronic renal failure can initiate the syndrome. Generally, the syndrome occurs most often in patients between the ages of 30 and 60 years and is five times more frequent in women than in men Milford, Lee., Campbell's Operative Orthopaedics., 7th Ed: 459). Clinical diagnosis is established by medical history, physical examination including the Phalen wrist flexion test Phelen, G. S.: The carpal tunnel syndrome: 17 years experience. J. Bone Joint Surgery., 48A:211-228, 1966) and Tinel's sign as well as the median nerve oompression test. Thenar atrophy to some degree may be evident with prolonged compression of the median nerve.

Carpal tunnel pressure measurements have been studied in symptomatic patients and such studies showed a marked increase in the mean pressure of the carpal tunnel from 32 mm with the wrist in neutral position to 99 mm with 90 degrees of flexion and 110 mm with the wrist in extension. Normal control measurements were 2.5 mm in neutral position, 31 mm in flexion, and 30 mm with wrist extension (Gelberman, R. H., Hergenroeder, P. T., Hargens, A. R., Lundborg, G. N., and Akerson, W. H.: The carpal tunnel syndrome: as study of carpal tunnel pressures, J. Bone Joint Surg. 65-A:380, 1981).

Electromyelographic studies in classical carpal tunnel syndrome show a distal wrist latency in conduction velocity. Prolongation of the distal sensory latency above 3.5 Msec has been found to be present in 85 to 95 per cent of surgically confirmed cases (Heckler, F. R., Jabaley, M. D.: Evolving concepts of median nerve decompression in the carpal tunnel: Hand Clinics 2(4):723-726, 1986). Irreversible muscle damage is indicated by denervation potentials.

Historically, carpal tunnel syndrome has been treated nonsurgically by splinting of the affected hand and wrist, oral antiinflammatory medioation, and local steroid injection. If nonsurgical methods are unsuccessful surgical intervention is indicated.

Open surgical decompression of the carpal tunnel by division of the transverse carpal ligament was first described in 1930 by Learmonth. Open procedures generally entail a curved longitudinal incision ulnar to and parallel to the thenar crease. Taleisnik described an incision along the ulnar border of the ring finger axis (Taleisnik, J.: The palmar cutaneous branch of the median nerve and the approach to the carpal tunnel: An anatomical study; Bond Joint Surg, 55A: 1212, 1973). This incision may extended proximally to the wrist flexor crease. Angling the incision towards the ulnar aspect of the wrist helps to avoid cutting the palmar sensory cutaneous branch of the median nerve. This nerve is located in the interval between the palmaris longus and the flexor carpi radialis tendons. After division of the skin and subcutaneous tissue, the transverse carpal ligament is identified and divided along its ulnar border to avoid and to prevent injury to the median nerve or its recurrent branch.

Open surgical decompression of the median nerve is not without risks and complications (Kuschner, Stuart H, Brien, William W, et al.; Complications associated with carpal tunnel release; Orthopedic Review: April 1991; Vol XX; Number 4:346-351). Long term analysis of patients having surgical treatment for carpal tunnel syndrome have shown a failure rate as high as 19% (Kulick, Michael, I., D.D.S., M.D., et al.; Long-term analysis of patients having surgical treatment of carpal tunnel syndrome,; Jour of Hand Surg; 11A (1):59-66. 1986). A study noted in The Journal of the American Medical Association in April, 1991 found "the initial relief of open carpal tunnel surgery to be shadowed by significant scar pain and weakness in almost a third of subjects after 2 years." (Nancollas, Michael P.; Symptoms may return after carpal tunnel surgery; JAMA,; Vol 265, No 15, p 1922, April 17, 1991). Thirty percent of all patients in the study were rated with poor or fair result at an average of 5.5 years follow-up "57% of the patients in the study complained of return of some preoperative symptoms, most commonly pain, beginning an average of 2 years after surgery." (Nancollas, Michael P.; Symptoms may return after carpal tunnel surgery; JAMA,; Vol 265, No 15, p 1922, Apr. 17, 1991.)

Complications include continued pain and or numbness, hypersensitive scar, loss of grip strength, joint stiffness, adherence of flexor tendons, neuroma, injury to the median nerve or its' motor branch or digital nerve injury, damage to the palmar cutaneous nerve, vascular injury, palmar hematoma, infection, and possible reflex sympathetic dystrophy.

A retrospective analysis of 40 cases of reoperation for carpal tunnel syndrome found adhesions and fibrosis around the median nerve in the carpal canal in 36 cases. (Wadstroem, J., Nigst, H.,; Reoperation for carpal tunnel syndrome: a retrospective analysis of 40 cases; Ann. Chir. Main; 5:54-58, 986.)

Hand weakness with loss of grip strength can also be a problem. Carpal tunnel release produces an average widening of the transverse carpal arch of 2.7 mm. There is a direct relationship between widening of the carpal canal and decreased grip strength. The average decrease in grip strength is 12%. (Gartsman, Gary, M., Kovach, John, C., et al.; Carpal arch alteration after carpal tunnel release; J. Hand Surg. (AM.) 11-A:3-72-374, May, 1986.) Computerized tomographic (CT) studies of the carpal tunnel after transsection of the transverse carpal igament have shown that if the flexor retinaculum is not intact, the flexor tendons will bowstring palmarly while the wrist and fingers are flexed together, causing weakness of grip. Some authors have recommended the use of a firm postoperative compression dressing immobilizing the wrist in slight dorsal extension for 3 weeks to prevent prolapse of the flexor tendons. (Jessurun, W, Hillen, B, et al.; Carpal tunnel release: Postoperative care: Handchirurgie 20:39-40, January, 1988.)

Because of the concern over widening of the carpal arch with subsequent decrease in grip strength, following standard carpal tunnel release, Jakab and associates devised a technique employing reconstruction of the transverse carpal ligament. (Jakab, Emery, Ganos, Doreen, et al.; Carpal tunnel release: Postoperative care: Handchirurgie 20:39-40, January, 1988.) These authors stated that by reconstructing the transverse carpal ligament, the transverse carpal arch was stabilized affording protection to the median nerve and preventing potential bowstringing of the flexor tendons. By repairing the transverse carpal ligament the normal relationship of the carpal canal and its contents was restored and maintained.

Pre and post operative CT scanning of the wrist in carpal tunnel syndrome has been performed and has shown that postoperative decompression results in the regeneration of a much more flexible ligament, which allows the contents of the tunnel, to expand anteriorly. The divided transverse carpal ligament heals in a stretched or arched position allowing more room for the median nerve and flexor tendons. (Chaise, F., Roger, B.,; Pre-and post-operative CT scanning of the wrist in carpal tunnel syndrome; Rev Chir. Orthop.; 72:297-302' 1986.)

In recent years endoscopic techniques have been utilized to incise and divide the transverse carpal ligament, (Agee, John, M., et al.; Results of a study on the effectiveness of endoscopic release of the carpal tunnel; American Society for Surgery of the Hand, 45th annual meeting; Okutsu I, Ninomiya S, et al.; Endoscopic management of carpal tunnel syndrome; Arthroscopy: 7(1):11-18, 1989; Okutsu I, Ninomiya S, et al.; Measurement of pressure in the carpal canal before and after endoscopic management of carpal tunnel syndrome: J. Bone Joint Surg: 71A (5):679-683, 1989;Chow, J. D. : Endoscopic release of the carpal ligament: A new technique for carpal tunnel syndrome: Arthroscopy: 5(1): 19-24, 1989.) Attempts have been made to decrease the size of the surgical incision with the benefit of decreasing postoperative morbidity because hand strength returns more quickly and the hand is less tender. (Quote: John M. Agee, M.D.; Endoscopic carpal tunnel release gentler than open; Orthopedics Today: February, 1991; p.24) Refinements of endoscopic release of the carpal ligament have been evolving but complications with this procedure have been reported The complications include neuropraxia of the median and or ulnar nerve, digital nerve laceration, laceration of palmar vessels, laceration of flexor tendons, neuropraxia or laceration of the palmar cutaneous branch of the median nerve, palmar hematoma, adhesions of tendons, perineural fibrosis, bowstringing of flexor tendons with loss of grip strength, incomplete transaction of the carpal ligament with recurrence of symptoms and hypertrophic scar. (Resnick, Charles T., Miller, Brent, W.: Endoscopic carpal tunnel release using the subligamentous two-portal technique; Contemporary Orthopaedics, Vol: 22 (3), March, 1991:269-277.) A dual incision technique has been developed (Chow, James, C., Y.; Endoscopic release of the carpal ligament: A new technique for carpal tunnel syndrome; Arthroscopy: 7(1): 19-24, 1989) with attempt to further increase the safety and efficacy of the endoscopic procedure but the potential complications of surgically transsecting the transverse carpal ligaments remain evident. A recent study was reported where endoscopic carpal tunnel release was practiced on 13 fresh-frozen cadaver hands by surgeons who had "extensive" clinical endoscopic carpal tunnel surgery experience at three Boston, Massachusetts teaching hospitals. Complete release of the transverse carpal ligament was achieved in only five of the cadaver hands. Endoscopically, the incomplete release of the ligment occurred distally, "where concern about the superficial palmar arch may have caused hesitation." It was found that the fat pad between the transacted edges of the transverse carpal ligament obscures the view through the endoscope and neurovascular structures may not be directly observed. (Schwartz, Jr., J. Tphomas; Symptoms may return after carpal tunnel surgery; JAMA,; Vol 265, No 15, p. 1925, Apr. 17, 1991) It was concluded that, "the recurrence rate in patients undergoing endoscopic carpal tunnel release must be scrutinized long term in light of the high incidence of incomplete sectioning of the ligament and the narrow margin of safety". (Schwartz, Jr., J. Thomas; Symptoms may return after carpal tunnel surgery; JAMA; Vol 265, No 15, p. 1925, Apr. 17, 1991).

Various patents disclose devices for inserting or placing catheters within chosen parts of the human body. U.S. Pat. No. 4,655,214 discloses a soft inflatable introducer having a closed rounded distal tip sheath. After insertion and placement of the introducer with sheath adjacent to distal end of a catheter, the sheath is inflated and approximal end of the sheath is sealed to maintained it in expanded inflatable condition where catheter is being intubated. After the catheter has been intubated, a clamp of the sheath is opened to deflate the sheath into the introducer withdrawn. U.S. Pat. No. 4,645,491 discloses a catheter placement apparatus used in inserting a catheter to a preferred depth. The device is constructed of a surgical needle provided with a longitudinal window to which a catheter inserted in the needle can be viewed. The catheter has a colored patch of the same length as the window in the series of spaced visually distinct markings allowing the position of the catheter to be accurately located by lining the colored patch with the window and inserting the catheter until at least one mark appears in the window, to determine, the distance of the mark from the surface of the skin. U.S. Pat. No. 3,537,452 discloses a needle guard and beveled cutter for use with intravenous catheterization units. The device has a tubular body with a flat base and a longitudinally slotted top. The diameter of the tube is greater than the diameter of the needle contained therein. U.S. Pat. No. 3,592,193 discloses a removable needle guide to be used with a flexible catheter tube in withdrawing or introducing fluids relative to a body. The needle guide has winged handles associated therewith which provides controlled insertion and removing from the body with subsequent attachment from a flexible catheter tube. U S. Pat. No. 5,011,478 discloses an introducer set including a sheath and dilator formed with a smooth external shape. The distal end of the sheath is embedded in the dilator and formed in angle oblique to the longitudinal access of the introducer set. U.S. Pat. No. 3,559,643 discloses a catheter placement unit for insertion of a catheter into a body lumen through an incised opening in the lumen wall. The unit includes a longitudinally slit sheath having a catheter therein and an advancer connected to one end of the catheter, initially and axial alignment with the sheath to close the end of the sheath.

SUMMARY OF THE INVENTION

The present invention is concerned with a procedure termed, "Percutaneous Carpal Tunnel-Plasty" which employs a balloon catheter device with a nerve protector inserter and pressure gauge monitor. The balloon catheter is inserted percutaneously and is utilized to dilate and expand the transverse carpal ligament, through serial applications of fluid pressure while it is moved along the carpal tunnel, thereby increasing the diameter of the carpal tunnel, relieving compression of the median nerve and alleviating the symptoms of carpal tunnel syndrome.

Thus, percutaneous dilatation of the transverse carpal ligament increases the spatial diameter of the carpal tunnel and relieves pressure on the median nerve in the hand and wrist without the surgical and treatment problems previously discussed.

The objects and advantages of the present invention are that it expands and permanently dilates the transverse carpal ligament increasing the size of the carpal tunnel and decompresses the medial nerve. The median nerve, blood vessels and flexor tendons are protected by the protective grooved director with insertion of the balloon catheter device.

The position of the grooved director and balloon catheter device is monitored throughout the procedure by image intensifier or x-ray control.

Another object and advantage is that the invention avoids cutting the transverse carpal ligament which serves a protective purpose in the palm and avoids cicatrix formation in the carpal tunnel and perineural fibrosis of the medial nerve.

Additional objects and advantages of the invention are that the procedure can be performed with or without endoscopic assistance, pressure measurements can be measured and monitored throughout the procedure, the procedure is simple and safe and the incision is minimal with very cosmetic result.

In the accompanying drawings, there is shown an illustrative embodiment of the invention from which these and other of objectives, novel features and advantages will be readily apparent.

DETAILED DESCRIPTION OF THE INVENTION

Figure 1:
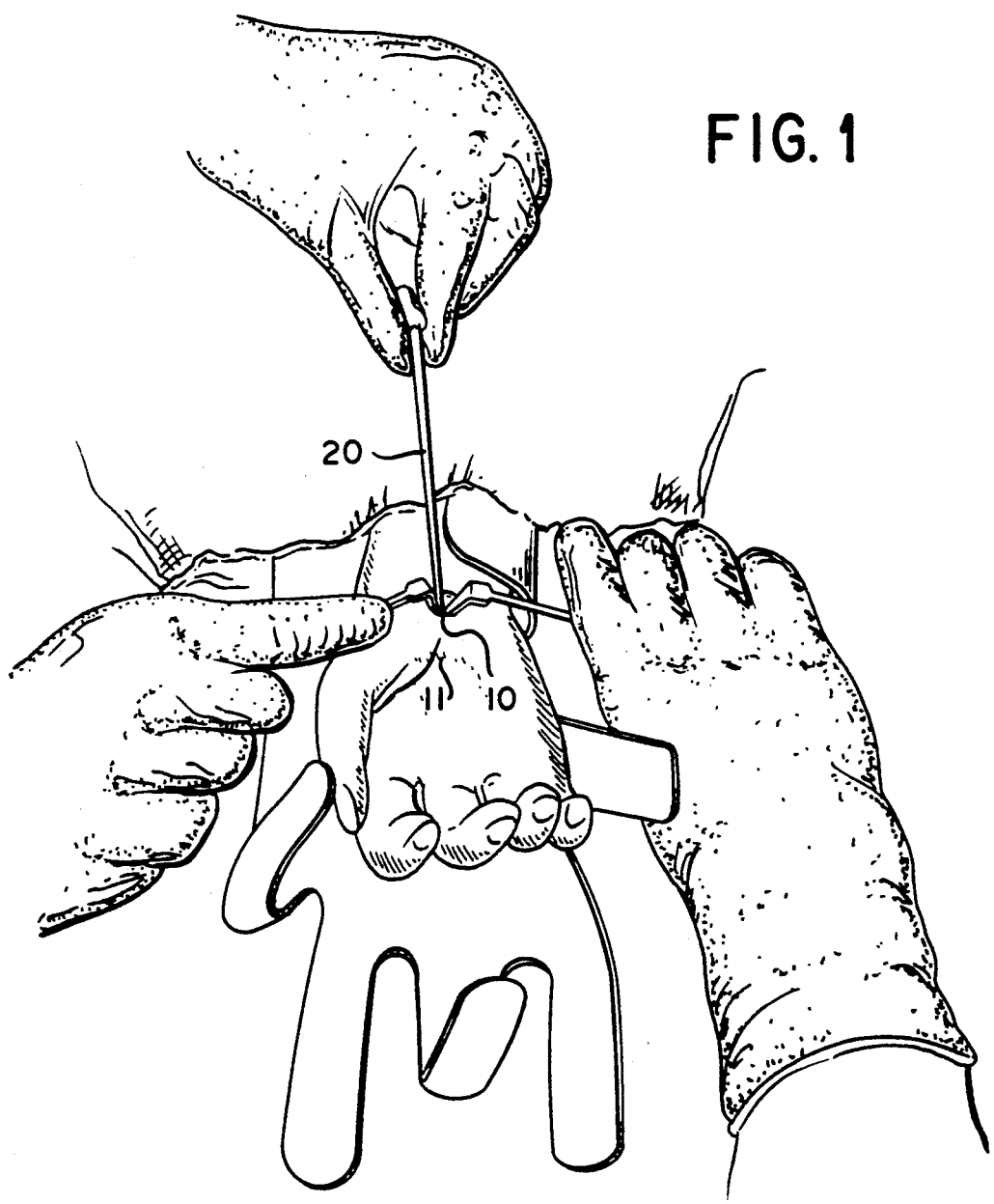
FIG. 1 is a perspective view of the inventive procedure after incision with the protective grooved director placed under the transverse carpal ligament directed an ulnar and superior direction to protect the median nerve and underlying structure.
Figure 2:
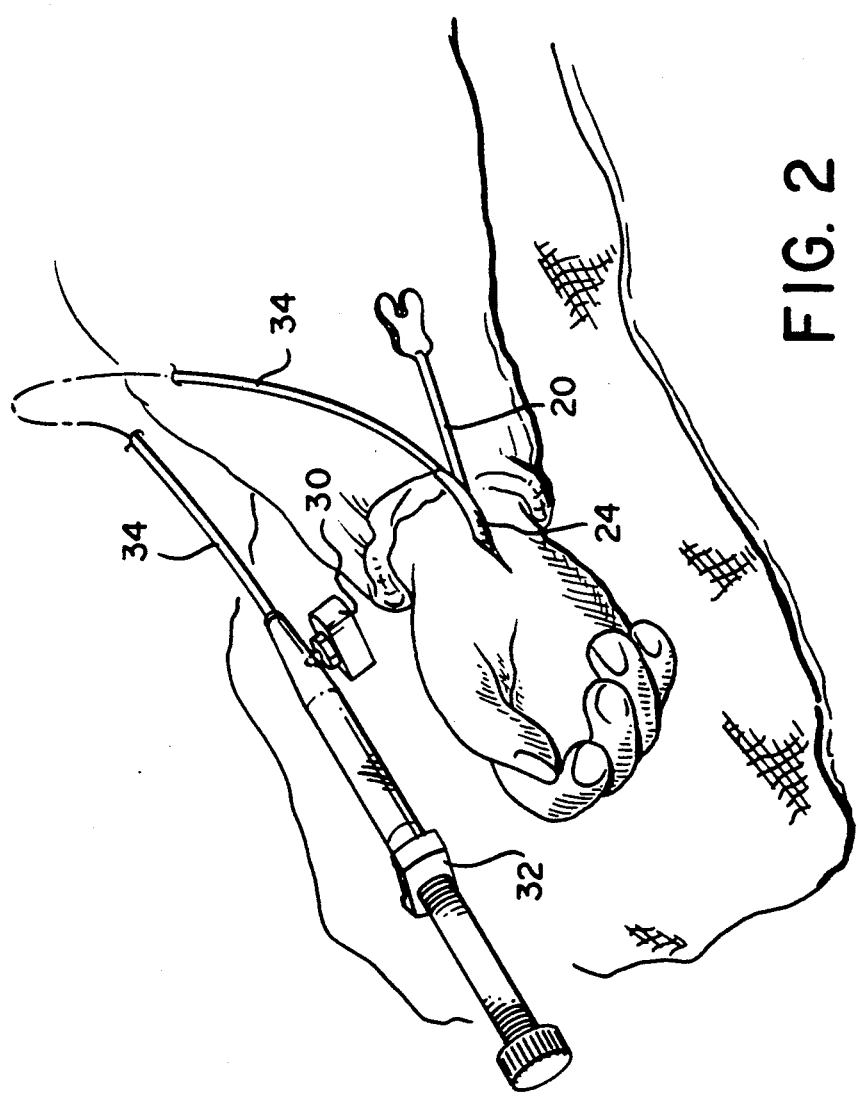
FIG. 2 is a perspective view of the inventive procedure showing insertion of the balloon catheter device in the grooved director.
Figure 3:
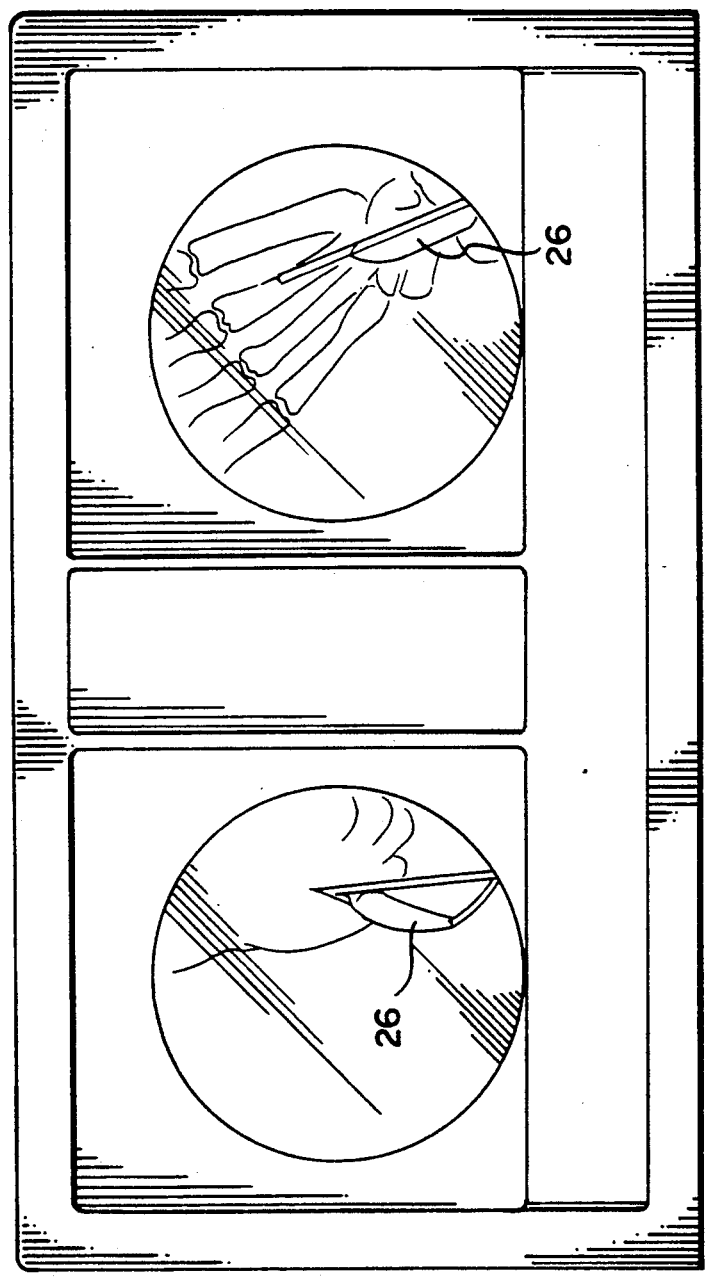
FIG. 3 is a view showing the protective grooved director in place with the balloon inflated to 10 mm diameter during the serial inflation and deflation of the balloon catheter.
Figure 4:
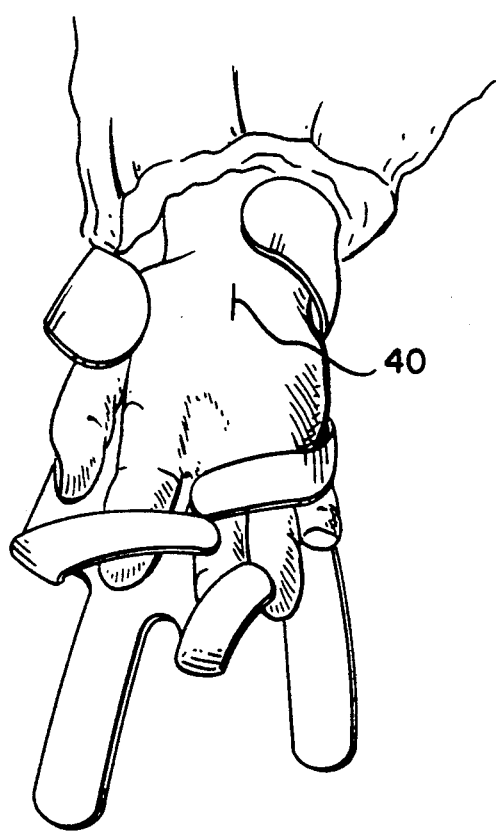
FIG. 4 is perspective view of the inventive procedure after removal of the protective grooved director and balloon catheter with the incision closed with a single structure.

A preferred embodiment and best mode of the invention is shown in FIGS. 1-4.

The patient is placed supine on the operating table. An intravenous Bier or axillary block is administered to the affected extremity. The upper extremity is then prepped and draped in the usual surgical fashion. A vertical one centimeter incision 10 is made just distal to the volar wrist crease in the mid-palm 11, overlying the median nerve. The incision is carried through the skin and subcutaneous tissue by sharp dissection. A self retaining retractor is placed in the wound. The most proximal portion of the transverse carpal ligament is identified. With care to protect the underlying median nerve, the protective carpal tunnel grooved director device 20 is placed underneath the transverse carpal ligament and inserted distally to the most distal margin of the transverse carpal ligament. A balloon catheter 24 is attached to the pressure monitor 30 and syringe 32. Initial pressure reading is taken of the carpal tunnel. Sterile saline solution is then injected from syringe 32 into the catheter 24 via tube 34 and the distal dilatation bulb or balloon 26 of the catheter is expanded in the most distal portion of the carpal canal. The position of the radioopaque catheter and balloon is confirmed by either image intensification or radiographs. The carpal tunnelplasty is performed by serially inflating and deflating the balloon catheter 24 intermittently along the course of the carpal tunnel from distal to proximal dilating and permanently stretching the transverse carpal ligament. Pressure measurements are taken throughout the procedure. The protective grooved device 20 serves to direct the balloon catheter in the carpal tunnel and protect the medial nerve and underlying structures. At the conclusion of the dilatation of the transverse carpal ligament, the balloon 26 is deflated and the catheter 24 and protective groove device 20 are removed. The tourniquet is released. The wound is irrigated with sterile saline solution. The subcutaneous layer is closed with a suture 40 and the skin is reapproximated. A sterile dressing is applied to the wound and the hand and wrist are splinted in 10 degrees of dorsiflexion.

EXAMPLE

A 50 year old, right hand dominant, white female presented with pain and paresthesias of the thumb, index and long fingers of the right hand.

The patient had a history of left carpal tunnel syndrome that had been treated previously by the inventor by open surgical carpal tunnel release. The patients hand pain and numbness of the fingers in the median nerve distribution of the left hand were satisfactorily relieved by the procedure but the patient complained of prolonged soreness at the incision site in the palm and some residual weakness of grip. Return to her normal activities of daily living were delayed after the open procedure.

The patient subsequently developed symptoms of carpal tunnel syndrome of her right hand characterized by tingling of the fingers, noctrunal pain, and weakness of grip. Thenar atrophy was minimal. Tinel's Phalen's test and the median nerve compression test were positive at the right wrist. Electrodiagnosic velocity across the wrist with prolongation of the distal sensory latency above 3.5 msec.. The patients pain became worse in spite of conservative measures including night splinting, anti-inflammatory medication, and local steroid injection.

The procedure of the present invention was performed in the operating room under strict aseptic conditions and regional IV Marcaine Bier Block to the right upper extremity. A 1cm longitudinal incision was made at the base of the right palm distal to the wrist crease, ulnar to the thenar eminance, in line with the ring finger axis. The proximal border of the transverse carpal ligament was identified by blunt dissection with care to avoid and protect the palmar cutaneous branch of the median nerve. The protective blunt tipped metal groove director 20 was then advanced under the ligament from proximal to distal direction, toward the ulnar aspect of the carpal tunnel, with care to identify and protect the underlying median nerve. The location and position of the protective goove director was confirmed by image intensifeier. A flexible undistended 10 mm balloon catheter device 24 was then guided through the groove on the superior aspect of the guide. Under image intensification control the balloon catheter 24 was inflated stretching the transverse carpal ligament. The balloom catheter was serially inflated and deflated along the course of the ligament from a distal to proximal direction. The median nerve remained protected throughout the procedure by the protective groove director 20. At the conclusion of the procedure the undersurface of the transverse carpal ligament was able to be inspected and found to be dilated and the median nerve was free of any constriction. The wound was closed with one simple suture 40 and a sterile dressing was applied with the hand splinted in 10 degrees of dorsiflexion. The patient tolerated the procedure well.

Post-operatively, the patient was discharged from the hospital on the day of surgery. Relief of preoperative pain and paresthesias of the right hand was immediate and complete. The patient had minimal tenderness at the incision site and was able to use the hand on the first post operative day. Preoperative grip strength of the right hand was 10 kg. Post operative grip strength was 30 kg. Grip strength for the nondominate post operative open surgical carpal tunnel release left hand was 18 kg.

It has been shown that standard oarpal tunnel release produces an average widening of the transverse arch of 2.7 mm. There is a direct relationship between widening of the canal and decreased grip strength. With Percutaneous Carpal Tunnel-Plasty the transverse carpal ligament is expanded and dilated. The transverse carpal arch remains stabilized preventing bowstringing of the flexor tendons. When the balloon catheter device is inflated, the protective grooved director has been designed to prevent compression on the median nerve and underlying structures. The median nerve remains protected avoiding cicatrix formation in the carpal tunnel and perineural fibrosis. The normal relationship of the carpal tunnel and its contents are maintained. The procedure can be performed with or without arthroscopic assistance. The position of the balloon catheter can be monitored with image or x-ray control. Pressure measurements can be taken and monitored during the procedure. There is a minimal skin inoision with very cosmetic result. The patient has less postoperative pain with a quick recovery time and earlier return to activities of daily living than can be obtained with open or endoscopic carpal tunnel release.

In the foregoing description, the invention has been described with reference to a particular preferred embodiment, although it is to be understood that specific details shown are merely illustrative, and the invention may be carried out in other ways without departing from the true spirit and scope of the following claims.

What is claimed:

1. A surgical procedure for relieving nerve entrapment syndrome by increasing the spatial diameter of the carpal tunnel enclosing the nerve comprising making an incision through the skin subcutaneous tissue proximate the .entrapped nerve, retracting the incision, inserting a director means for protecting the nerve and underlying structure into said incision, inserting a deflated balloon catheter by means of said director means through said incision into said tunnel along with means for monitoring pressure in said tunnel, serially inflating and deflating said balloon catheter while intermittently moving it along the tunnel and continuously montioring the pressure therein to thereby increase the diameter of the tunnel, deflating and removing said catheter, and director means from said incision and closing the incision.

2. The procedure of claim 1 wherein said procedure is continuously monitored optically.

3. The procedure of claim 1 wherein said balloon catheter is inflated by means of a liquid injected into it.

4. The procedure of claim 1 wherein said means for monitoring pressure is a pressure gauge.

5. The procedure of claim 1 wherein the transverse carpal ligament is expanded and dilated to increase the diameter of a carpal tunnel.

6. The procedure of claim 1 wherein said nerve is the median nerve.

7. A surgical procedure for decompressing the median nerve in the carpal tunnel by increasing the spatial diameter of the carpal tunnel enclosing the median nerve which comprises making an incision through the skin and subcutaneous tissue proximate the median nerve, retracting the incision, identifying the proximal portion of the transverse carpal ligament, inserting a grooved director means for protecting the nerve and carpal ligament into said incision, inserting a deflated balloon catheter by means of said director means through said incision along with pressure monitoring means underneath the transverse carpal ligament to the most distal end thereof; injecting a fluid into said balloon catheter and serially inflating and deflating said catheter while intermittantly moving it along said carpal tunnel from distal to proximal end and continuously monitoring the pressure therein thereby stretching the transverse carpal ligament, deflating and removing said catheter, director means and pressure monitoring means from said incision and closing the incision.

8. The surgical procedure of claim 7 wherein said procedure is monitored optically.

9. The surgical procedure of claim 8 wherein said optical monitoring is by means of image intensification or radiography.

* * * * *